United States Patent [19]

Müller

[11] Patent Number: 4,954,345
[45] Date of Patent: Sep. 4, 1990

[54] DERMALLY ACTING PHARMACEUTICAL PREPARATION WITH LIPOSOMES AS VEHICLE MEANS

[75] Inventor: Joseph Müller, Lindenfels, Fed. Rep. of Germany

[73] Assignee: Rohm Pharma GmbH, Weiterstadt, Fed. Rep. of Germany

[21] Appl. No.: 232,545

[22] Filed: Aug. 15, 1988

Related U.S. Application Data

[63] Continuation of Ser. No. 924,014, Oct. 28, 1986, abandoned.

[30] Foreign Application Priority Data

Dec. 4, 1985 [DE] Fed. Rep. of Germany ....... 3542773

[51] Int. Cl.$^5$ ...................... A61K 9/127; A61K 37/22
[52] U.S. Cl. .................................... 424/450; 264/4.6; 428/402.2; 514/861; 514/887; 514/937; 514/947; 514/969
[58] Field of Search ..................... 428/402.2; 424/450; 436/829; 514/861, 862, 887, 947, 969

[56] References Cited

U.S. PATENT DOCUMENTS 3,957,971  5/1976  Oleniacz ..................... 252/DIG. 13
4,427,649  1/1984  Dingle et al. ........................ 424/450
4,438,052  3/1984  Weder et al. ......................... 264/4.6

FOREIGN PATENT DOCUMENTS 0152414  8/1985  Japan ................................. 424/450

*Primary Examiner*—Richard D. Lovering
*Attorney, Agent, or Firm*—Oblon, Spivak, McClelland, Maier & Neustadt

[57] ABSTRACT

The present invention is directed to a pharmaceutical preparation for external or transdermal application which comprises a dispersion of liposomes, wherein said liposomes incorporate or enclose an active ingredient.

13 Claims, No Drawings

DERMALLY ACTING PHARMACEUTICAL PREPARATION WITH LIPOSOMES AS VEHICLE MEANS

This application is a continuation of application Ser. No. 924,014, filed on Oct. 28, 1986, now abandoned.

BACKGROUND OF THE INVENTION

1. Field of the Invention:

The invention relates to medicaments for therapy of skin disorders. These medicaments may include materials which are known for the treatment of skin disorders, and are used as external topical agents on the skin. The invention also relates to medicaments for non-skin disorders, in which the medicaments are applied transdermally.

2. Discussion of the Background:

As a rule, ointments, creams, lotions or tinctures which incorporate specific active ingredients, are used topically for skin disorders. A prerequisite for the therapeutic effectiveness of these active ingredients is that they are liberated in therapeutic amounts from the respective matrix. Only if this occurs can the active ingredients penetrate into the skin and from there reach the sites at which their activity is required.

Liposomes are novel medicinal vehicles. Liposomes are defined as spheroidal structures comprised of one or more lipid double layers, and having an aqueous interior cavity. They may be prepared from phospholipids, for example, lecithin by mechanical breakdown to produce fine particles. Techniques for preparing liposomes, and use of liposomes as pharmaceutical or cosmetic vehicles with the active ingredients deposited in the interior cavities of the liposomes, are described in U.S. Pat. No. 3,957,971, German No. OS 28 18 655, German No. OS 28 34 308 and British Pat. No. 2,013,609. The state of the art in 1982 regarding the preparation of liposomes and their use as pharmaceutical vehicles is disclosed in *Pharmazie in unserer Zeit* 11:97-108 (1982). According to the latter article, application of pharmaceutical-containing liposomes has been tested by intravenous, intramuscular, and subcutaneous injections, and also by oral administration.

There is, therefore, a prejudice in the art against the testing of medicinal formulations using liposomes as the vehicle wherein such formulations are applied locally on the skin, e.g., topical application in skin disorders. This is based on the knowledge of skin structure and extensive experience with skin application. Specifically, the prejudice against topical application relates to the presence, underneath the stratum corneum (the horny superficial layer of the skin), of a denser layer of cells, the stratum conjunctum or stratum compactum, having the function of impeding penetration or substances from the exterior.

The most frequently used active ingredients in external treatment of skin disorders are corticosteriods and trihydroxyanthracenes. However, these materials have low penetrability through the skin after being liberated from their vehicles. Therefore, when they are employed in, for example, ointments or creams they must be present in relatively high concentration and large excess in order to achieve an adequate therapeutic effect.

SUMMARY OF THE INVENTION

Accordingly, an object of the present invention is to provide a vehicle means which is effective for dermally acting pharmaceutical substances, whereby the active ingredients can penetrate into and through the skin so that the active ingredients are provided continuously and in sufficient quantity at the site of action.

Another object of the present invention is to provide a pharmaceutical preparation which is effective for the treatment of skin disorders and in which a relatively high concentration and large excess of the active ingredient is not required for effective treatment.

Still a further object of the invention is to provide a pharmaceutical preparation comprising an active ingredient for non-skin disorders which can be administered transdermally.

These objects and other objects of the present invention which will become apparent from the following specification have been achieved by the novel dermally acting pharmaceutical preparation of the present invention which comprises a dispersion, wherein at least one active ingredient is in dissolved, emulsified or suspended form, and wherein said active ingredient is incorporated or enclosed in liposomes.

DETAILED DESCRIPTION OF THE PREFERRED EMBODIMENTS

It has been discovered that dermally acting pharmaceuticals such as, for example, corticosteroids and trihydroxyanthracenes, combine relatively readily with liposomes, i.e., they can be incorporated or enclosed in liposomes. Surprisingly, it has been discovered that liposomes which have pharmaceuticals thus incorporated or enclosed in them and which are applied to the skin in the form of a spreadable surface-application, e.g., an ointment or cream, promote substantially more rapid penetration of the active ingredients than ordinary ointment formulations of the active ingredients.

It has further been discovered that urea, which has a number of known qualities for therapy of skin disorders, for example, as a keratolytic, can also be taken up in liposomes. Advantageous mixtures of urea and other dermally acting pharmaceutical substances, such as the steroids and/or trihydroxyanthracenes noted above can be formulated with liposomes or with phospholipid mixtures (which are precursors to liposomes) to produce dermally acting medications.

Penetrations of 5-10 times those of previously widely used formulations were measured with the abovementioned liposome medications. With known applications of corticosteroids, the amount which penetrates the skin is only at most 5-10% of the locally applied amount. The novel formulations thus enable savings of substantial quantities of active ingredient. This in turn alleviates or eliminates other problems, for example, the soiling of textiles which occurs when colored substances or colored metabolites (e.g., oxidation products of trihydroxyanthracenes) are present.

Various methods may be employed to prepare the inventively applied liposome preparations from the components of the liposomes, namely phospholipids. Particularly suitable phospholipids are phosphatidylcholines, such as lecithins (a naturally occurring group of phospholipids). Lecithin from soybeans is the most common raw material for producing lecithin. To these components certain additives are added, such as sterols, e.g., cholesterol, and the dermally acting pharmaceutical substance. The methods used may be those described, for example, in the abovementioned literature references.

The ratio of the substances in the initial lipid mixture used for preparing the liposome vehicle, namely the ratio of lecithin to cholesterol, may be in the range 10:0.1 to about 1:1, especially 10:1 to 1:1, and particularly 5:1 to 2:1. Additional substances such as dialkyl phosphates or sphingomyelin, or adjuvants such as sugar derivatives or amino sugar derivatives for stabilizing the liposome membranes and antioxidants, may also be used in the preparation.

The preparation may be carried out according to the known film dispersion method, comprising careful evaporative concentration of the mixture of lipids and active ingredients, in a chloroform/alcohol solution. A rotary evaporator may be used and may be followed by treatment with ultrasound for producing particularly small particles with a relatively narrow size distribution. The liposomes, which contain the active ingredient, can then be isolated and purified by centrifuging and washing. The particle sizes of the liposomes produced by such methods can vary over a wide range, from several microns down to about 10 nm. Preferably, for use as vehicles for dermally acting pharmaceutical substances, the liposomes should have diameters of 20-50 nm.

Active ingredients which form the dermally acting pharmaceutical preparations of the present invention may belong to the large groups comprising the antibiotics or sulfonamides, and particularly the groups comprising the corticosteroids and the hydroxyanthracenes. The therapeutic effects of these materials are known, particularly in treatment of inflammatory, eczematous, and allergic skin disorders. Increased therapeutic effectiveness can be obtained by combining active ingredients from the different substance groups.

Also, the use of urea in preparing active ingredient-containing liposomes in combination with hydroxyanthracenes and/or corticosteroids leads to therapeutically valuable formulations. The advantage of the inventive medicaments over known medicaments with the same active ingredients lies in the improved penetration through the skin, hence higher availability of the medicine at the site of action, and thereby an appreciable reduction in the amount of active ingredient which must be used. This in turn is reflected in reduced side effects and a substantial reduction in the cost of the medicament.

Non-limiting examples of corticosteroids which may be used according to the invention include fluorocortisone, fluocortolone, fluorandrenolene, triamcinolone, and methylprednisolone. Trihydroxyanthracenes which may be used in the inventive formulations and which are known to be dermatics or antiseptics are 1,8,9-trihydroxyanthracene (also known as dithranol) and 1,2,10-trihydroxyanthracene.

The use of medicaments in liposomes increases the effectiveness of transdermal administration of active ingredients of various types for disorders of body parts other than the skin or regions near the skin. This is due to improved skin penetration and therefore, more rapid transport of the pharmaceutical.

The preparations may also contain active ingredients for which skin penetration is not indicated or for which the rate of skin penetration is not very critical. The amounts of such active ingredients are those commonly used in past practice.

The preparations for external application to the skin are dispersions which contain the active ingredients and liposomes as prepared, and any added ingredients, in dissolved, emulsified, or suspended form. The manner of applying the novel dermally acting medicaments with pharmaceutical-containing liposomes is essentially the known methods, e.g., as ointments or creams.

Other features of the invention will become apparent in the course of the following descriptions of exemplary embodiments which are given for illustration of the invention are not intended for be limiting thereof.

EXAMPLES

1. Preparation of Combinations of Active Ingredients and Liposomes

Solutions of lecithin, cholesterol, and an active ingredient in chloroform/ethanol (1:1) or in chloroform/methanol (1:1) were evaporatively concentrated at about 30° C. in a rotary evaporator, whereby a thin film of lipid and active ingredients formed. Then, 8M calcium chloride solution at 60° C. was added to the film, and the liposomes were separated from the wall by manual shaking. The resulting dispersion was then placed in an ultrasonic disintegrator, to produce smaller particle sizes and was centrifuged. The combination of liposomes and active ingredient was then washed 3 times with calcium chloride solution.

The following Table gives the compositions of the liposomes produced, as parts by weight, and the percentage of active ingredient (triamcinolone or dithranol) which was incorporated in the liposomes.

TABLE 1

| Sample No. | 1 | 2 | 3 | 4 | 5 | 6 |
|---|---|---|---|---|---|---|
| Lecithin (parts by wt.): | 30 | 30 | 32.5 | 32.5 | 35 | 35 |
| Cholesterol (parts by wt.): | 13 | 10 | 13 | 10 | 10 | 7 |
| % of triamcinolone incorporated: | 41 | 32.4 | 56.2 | 42.8 | 62.1 | 49.8 |
| % of dithranol incorporated: | 69.7 | 42.1 | 85.6 | 76.1 | 87.5 | 62.1 |

2. Comparison of Penetrations of Active Ingredients

Penetration Tests were performed with isolated skin, measuring penetration into a penetration chamber.

Triamcinolone Acetonide
Penetration from a 0.1% preparation, in 6 hr:
8.26% without liposomes.
28.60% with liposomes.
Dithranol
Penetration from a 0.1% preparation, in 100 min:
Ratio of (without liposomes): (with liposomes) = 1:8

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A dermally acting pharmaceutical preparation for external application to the skin, consisting essentially of:
   a dispersion, wherein said dispersion comprises urea and at least one active ingredient selected from the group consisting of corticosteroids and trihydroxyanthracenes and is in dissolved, emulsified or suspended form, and wherein said urea and said active ingredient are incorporated or enclosed in liposomes.

2. The preparation of claim 1, wherein said active ingredient is useful for the treatment of skin disorders.

3. The preparation of claim 1, wherein said active ingredient is a corticosteroid.

4. The preparation of claim 3, wherein said corticosteroid is a member selected from the group consisting of fluorocortisone, fluorocortolone, fluoroandrenolone, triamcinolone and methylprednisolone.

5. The preparation of claim 4, wherein said corticosteroid is triamcinolone.

6. The preparation of claim 1, wherein said active ingredient is a trihydroxyanthracene.

7. The preparation of claim 6, wherein said trihydroxyanthracene is 1,2,10-trihydroxyanthracene or dithranol.

8. The preparation of claim 7, wherein said trihydroxyanthracene is dithranol.

9. The preparation of claim 1, wherein said liposomes contain one or more corticosteroids and dithranol.

10. The preparation of claim 1, wherein said active ingredient is useful for treating non-skin disorders.

11. The preparation of claim 1, further comprising additional ingredients selected from the group consisting of sterols, dialkyl phosphates, sphingomyelin, antioxidants, sugar derivatives and amino sugar derivatives.

12. A method of treating skin disorders, comprising contacting skin with the pharmaceutical preparation of claim 1.

13. A method of treating non-skin disorders comprising transdermal administration of the pharmaceutical preparation of claim 1.

* * * * *